US009761678B2

(12) United States Patent
Moser et al.

(10) Patent No.: US 9,761,678 B2
(45) Date of Patent: Sep. 12, 2017

(54) GALLIUM ARSENIDE HETEROJUNCTION SEMICONDUCTOR STRUCTURE

(71) Applicant: RF Micro Devices, Inc., Greensboro, NC (US)

(72) Inventors: Brian G. Moser, Jamestown, NC (US); Michael T. Fresina, Greensboro, NC (US)

(73) Assignee: Qorvo US, Inc., Greensboro, NC (US)

( * ) Notice: Subject to any disclaimer, the term of this patent is extended or adjusted under 35 U.S.C. 154(b) by 486 days.

(21) Appl. No.: 13/655,659

(22) Filed: Oct. 19, 2012

(65) Prior Publication Data

US 2013/0099287 A1 Apr. 25, 2013

Related U.S. Application Data

(60) Provisional application No. 61/549,316, filed on Oct. 20, 2011.

(51) Int. Cl.
  *H01L 29/66* (2006.01)
  *H01L 29/417* (2006.01)
  (Continued)

(52) U.S. Cl.
  CPC .... *H01L 29/41708* (2013.01); *H01L 29/0817* (2013.01); *H01L 29/42304* (2013.01);
  (Continued)

(58) Field of Classification Search
  CPC . H01L 29/0817; H01L 29/201; H01L 29/205; H01L 29/207; H01L 29/41708;
  (Continued)

(56) References Cited

U.S. PATENT DOCUMENTS 6,737,684 B1 * 5/2004 Takagi et al. .............. 257/194
7,019,383 B2 3/2006 Zampardi et al.
(Continued)

OTHER PUBLICATIONS

Mochizuki et al., "GaInP/GaAs Collector-Up Tunneling-Collector Heterojunction Bipolar Transistors (C-Up TC-HBTs): Optimization of Fabrication Process and Epitaxial Layer Structure for High-Efficiency High-Power Amplifiers," IEEE Transactions on Electron Devices, vol. 47, No. 12, Dec. 2000, pp. 2277-2283.
(Continued)

*Primary Examiner* — Mohammed Shamsuzzaman
(74) *Attorney, Agent, or Firm* — Withrow & Terranova, P.L.L.C.

(57) ABSTRACT

Embodiments of semiconductor structure are disclosed along with methods of forming the semiconductor structure. In one embodiment, the semiconductor structure includes a semiconductor substrate, a collector layer formed over the semiconductor substrate, a base layer formed over the semiconductor substrate, and an emitter layer formed over the semiconductor substrate. The semiconductor substrate is formed from Gallium Arsenide (GaAs), while the base layer is formed from a Gallium Indium Nitride Arsenide Antimonide (GaInNAsSb) compound. The base layer formed from the GaInNAsSb compound has a low bandgap, but a lattice that substantially matches a lattice constant of the underlying semiconductor substrate formed from GaAs. In this manner, semiconductor devices with lower base resistances, turn-on voltages, and/or offset voltages can be formed using the semiconductor structure.

4 Claims, 24 Drawing Sheets

(51) Int. Cl.
*H01L 29/423* (2006.01)
*H01L 29/737* (2006.01)
*H01L 29/08* (2006.01)
*H01L 29/201* (2006.01)
*H01L 29/205* (2006.01)
*H01L 29/207* (2006.01)

(52) U.S. Cl.
CPC .... *H01L 29/66318* (2013.01); *H01L 29/7371* (2013.01); *H01L 29/201* (2013.01); *H01L 29/205* (2013.01); *H01L 29/207* (2013.01)

(58) Field of Classification Search
CPC ......... H01L 29/42304; H01L 29/66318; H01L 29/737
USPC .............. 257/197, 192, 194, 474, 200, 184; 438/312, 478, 509, 376
See application file for complete search history.

(56) References Cited

U.S. PATENT DOCUMENTS

| | | | |
|---|---|---|---|
| 7,186,624 B2 | 3/2007 | Welser et al. | |
| 7,242,038 B2* | 7/2007 | Oda et al. | 257/197 |
| 7,656,002 B1* | 2/2010 | Barratt et al. | 257/474 |
| 2002/0070390 A1* | 6/2002 | Chow | 257/197 |
| 2005/0139863 A1* | 6/2005 | Welser et al. | 257/197 |
| 2009/0014061 A1 | 1/2009 | Harris, Jr. et al. | |
| 2011/0232730 A1* | 9/2011 | Jones et al. | 136/255 |

OTHER PUBLICATIONS

Geisz et al., "III-N-V Semiconductors for Solar Photovoltaic Applications," Figure 2, Semiconductor Sci. Technol., vol. 17, 2002, 1 page.

Yan et al., "Low Turn-on Voltage InGaP/GaAsSb/GaAs Double HBTs Grown by MOCVD," IEEE Electron Device Letters, vol. 23, No. 4, Apr. 2002, pp. 170-172.

Welser et al., "Turn-on Voltage Investigation of GaAs-Based Bipolar Transistors with Ga1-xInxAs1-yNy Base Layers," IEEE Electron Device Letters, vol. 21, No. 12, Dec. 2000, pp. 554-556.

Deluca et al., "Implementation of Reduced Turn-on Voltage InGaP HBTs Using Graded GaInAsN Base Regions," IEEE Electron Device Letters, vol. 23, No. 10, Oct. 2002, pp. 582-584.

Yarborough, et al., "Enhanced CDMA Performance from an InGaP/InGaAsN/GaAs N-p-N Double Heterojunction Bipolar transistor," GaAs IC Symposium Digest, 2002, pp. 273-276.

Liu, "Handbook of III-V Heterjunction Bipolar Transistors," John Wiley & Sons 1998, pp. 147.

Kurtz et al., "InGaAsN solar cells with 1.0eV bandgap, lattice matched to GaAs," Applied Physics Letters, vol. 74, No. 5, Feb. 1999, pp. 729-731.

Ptak et al., "Low-acceptor-concentration GaInNAs grown by molecular-beam epitaxy for high current p-i-n solar cell applications," Applied Physics Letters, vol. 98, 2005, 5 pages.

Jackrel et al., "Dilute nitride GaInNAs and GaInNAsSb solar cells by molecular beam epitaxy," Journal of Applied Physics, vol. 101, 2007, 8 pages.

Yuen et al., "The role of antimony on properties of widely varying GaInNAsSb compositions," Journal of Applied Physics, vol. 99, 2006, 8 pages.

Stockman et al., "Growth of carbon-doped p-type InxGa1-xAs ($0 < x \leq 0.53$) by metalorganic chemical vapor deposition," Applied Physics Letters, vol. 60, No. 23, Jun. 1992, pp. 2903-2905.

Cai et al., "Heavily carbon-doped In0.53Ga0.47As on InP (001) substrate grown by solid source molecular beam epitaxy," Journal of Vacuum Science Technology B., vol. 17, No. 3, May/Jun. 1999, pp. 1190-1194.

* cited by examiner

GALLIUM ARSENIDE HETEROJUNCTION SEMICONDUCTOR STRUCTURE

RELATED APPLICATIONS

This application claims the benefit of provisional patent application Ser. No. 61/549,316, filed Oct. 20, 2011, the disclosure of which is hereby incorporated herein by reference in its entirety.

FIELD OF THE DISCLOSURE

This disclosure relates generally to semiconductor structures.

BACKGROUND

Semiconductor materials with narrow bandgaps are often sought to form the base layers of Gallium Arsenide (GaAs) heterojunction bipolar transistors (HBTs) in order to produce lower base resistances, turn-on voltages ($V_{be,on}$), and offset voltages ($V_{ce}$ when $I_{ce}$~=0). In theory, a reduction in the offset voltage would also reduce the knee voltage and should provide Power Added Efficiency (PAE) improvements in a power amplifier application. However, the choice of available base materials is generally limited by the constraints of matching the lattice constant of the underlying GaAs substrate.

Poor lattice matching between layers in the semiconductor structure often results in lattice stresses that degrade performance. For example, $Ga_{0.95}In_{0.05}N_{0.003}As_{0.997}$ has been used as base material to reduce the turn-on voltage and offset voltage of an HBT while maintaining a usable current gain β of the HBT. Both Gallium Arsenide Antimonide (GaAsSb) and Gallium Indium Arsenide (GaInAs) have also been used as base materials in Indium Gallium Phosphide (InGaP) HBTs. These base materials did lower turn-on voltages, but resulted in lower current gains β due to higher base resistances.

Accordingly, semiconductor materials with narrow bandgaps less than GaAs are needed to provide lower base resistances, turn-on voltages, and/or offset voltages while providing adequate lattice matching with the underlying GaAs substrate.

SUMMARY

Embodiments of semiconductor structures are disclosed, along with methods of forming the semiconductor structures. In one embodiment, the semiconductor structure includes a semiconductor substrate, a collector layer formed over the semiconductor substrate, a base layer formed over the semiconductor substrate, and an emitter layer formed over the semiconductor substrate. The semiconductor substrate is formed from Gallium Arsenide (GaAs), while the base layer is formed from a Gallium Indium Nitride Arsenide Antimonide (GaInNAsSb) compound. The base layer formed from the GaInNAsSb compound has a low bandgap, but a lattice that substantially matches a lattice constant of the underlying semiconductor substrate formed from GaAs. In this manner, semiconductor devices with lower base resistances, turn-on voltages, and/or offset voltages can be formed using the semiconductor structure.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWING FIGURES

The accompanying drawing figures incorporated in and forming a part of this specification illustrate several aspects of the disclosure, and together with the description serve to explain the principles of the disclosure.

DETAILED DESCRIPTION

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

Figure 1:
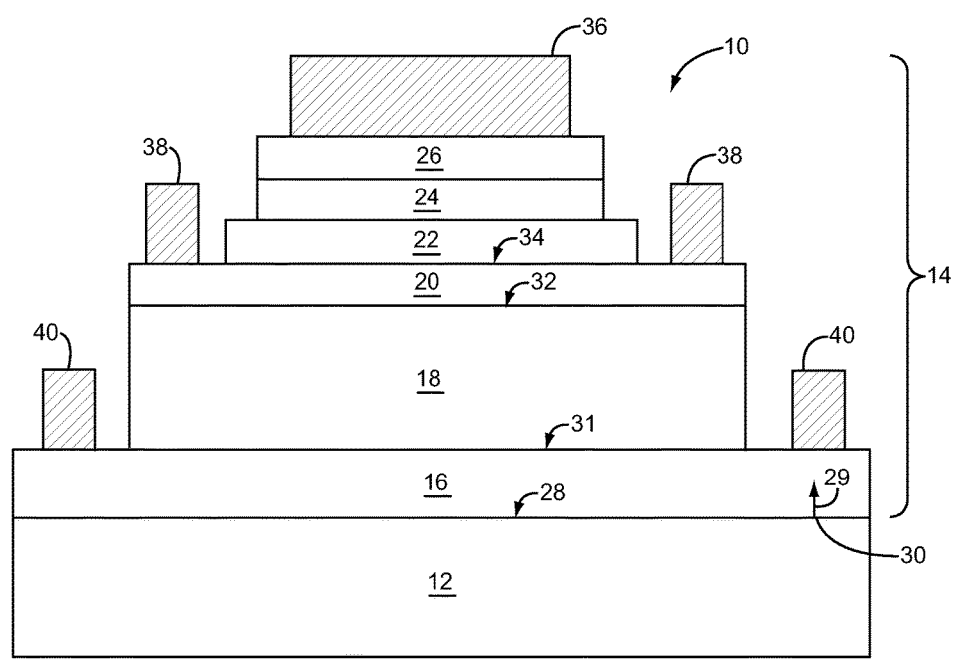
FIG. 1 illustrates one embodiment of a semiconductor structure having a semiconductor substrate formed from Gallium Arsenide (GaAs), a collector layer, a base layer, and an emitter layer, where the base layer is formed from a Gallium Indium Nitride Arsenide Antimonide (GaInNAsSb) compound and where a heterojunction bipolar transistor (HBT) has been formed with the semiconductor structure.

FIG. 1 illustrates one embodiment of a semiconductor structure 10 that has a lower base resistance, a lower turn-on voltage, and a lower knee voltage when compared with other known Gallium Arsenide (GaAs)—type structures. A body of the semiconductor structure 10 is provided by a semiconductor substrate 12. The semiconductor substrate 12 is formed from GaAs. The semiconductor substrate 12 may have a thickness of anywhere from approximately 10 micrometers to several hundred micrometers.

The semiconductor substrate 12 is a crystalline solid whose molecules are arranged in an ordered pattern (excluding defects) with respect to three orthogonal spatial dimensions. As such, the semiconductor substrate 12 may be formed from a GaAs crystal where the GaAs molecules of the GaAs crystal form a solid material and have a generally periodic arrangement. The lattice of the GaAs crystal is body-centered cubic and thus the distance between unit cells in the GaAs crystal are the same in all three orthogonal spatial directions. Accordingly, the GaAs crystal has a lattice constant that describes the constant distance in all three orthogonal spatial dimensions between the unit cells of the GaAs crystal.

An epitaxial region 14 is provided over the semiconductor substrate 12. Semiconductor devices with desired functional characteristics may be provided in the epitaxial region 14. In this embodiment, the epitaxial region 14 has been formed to provide a heterojunction bipolar transistor (HBT). However, it should be noted that, in other embodiments, any type of suitable semiconductor device may be formed in the epitaxial region 14.

The epitaxial region 14 includes a subcollector layer 16, a collector layer 18, a base layer 20, an emitter layer 22, a grading layer 24, and an emitter cap layer 26, each formed over the semiconductor substrate 12. Note that in alternative embodiments, the semiconductor structure 10 may simply include the collector layer 18, the base layer 20, and the emitter layer 22. Different types of layers (such as insulating layers) may be provided additionally and/or alternatively to the subcollector layer 16, the grading layer 24, and the emitter cap layer 26. In fact, the semiconductor structure 10 may have any type of arrangement, which may, for example, depend on the semiconductor device or semiconductor devices to be built in the epitaxial region 14.

As shown in FIG. 1, the semiconductor substrate 12 has a surface 28, where the epitaxial region 14 is formed on the surface 28. The surface 28 thus defines a direction 29 normal to the surface 28. Terms in this disclosure referring to directional words such as "over" or "top" and "under" or "beneath" are made with respect to the direction 29 defined by the surface 28 of the semiconductor substrate 12. Thus, the epitaxial region 14 is formed over the semiconductor substrate 12, since the structures of the epitaxial region 14 extend in the direction 29. However, the subcollector layer 16 is under the collector layer 18, for example, because the subcollector layer 16 extends in a direction opposite the direction 29 with respect to the collector layer 18.

The subcollector layer 16, the collector layer 18, the base layer 20, the emitter layer 22, the grading layer 24, and the emitter cap layer 26 are formed so as to be substantially parallel to one another. This simply means that the subcollector layer 16, the collector layer 18, the base layer 20, the emitter layer 22, the grading layer 24, and the emitter cap layer 26 are stacked and extend in about the same direction. The types of semiconductor materials that may be formed over the semiconductor substrate 12 generally need to match the lattice constant of the GaAs crystal that forms the semiconductor substrate 12. If there is insufficient lattice matching between the GaAs crystal of the semiconductor substrate 12 and the materials forming the epitaxial region 14, the semiconductor materials in the epitaxial region 14 become strained and, in some circumstances, may not function appropriately.

While there are techniques for grading between the lattices of different semiconductor materials, this is not always possible if the lattice differences are sufficiently extreme. Also, even when these techniques are available, grading techniques can be difficult to implement, and are therefore costly. It would be simple to form each layer in the epitaxial region 14 from GaAs. However, GaAs has limited electrical capabilities. Thus, different types of semiconductor materials are needed to provide better performance while maintaining the lattice match with the semiconductor substrate 12.

Accordingly, the base layer 20 is formed from a Gallium Indium Nitride Arsenide Antimonide (GaInNAsSb) compound. The base layer 20 may be epitaxial such that the GaInNAsSb compound is a GaInNAsSb crystal. The GaInNAsSb crystal has a lattice constant that substantially matches the lattice constant of the GaAs crystal of the semiconductor substrate 12. Accordingly, the base layer 20 can be formed to have a crystalline structure with an acceptable number of crystallographic defects and without requiring additional grading. In one embodiment, the GaInNAsSb crystal that forms the base layer 20 has a non-stochiometric formula of $Ga_{1-x}In_xN_yAs_{1-y-z}Sb_z$, $0.07 \leq x \leq 0.18$, $0.025 \leq y \leq 0.04$, $0.001 \leq z \leq 0.03$.

The GaInNAsSb crystal of the base layer 20 may be doped such that the base layer 20 is p-type. The semiconductor substrate 12 is not doped and is semi-insulating. While the GaInNAsSb crystal provides lattice matching with the GaAs crystal of the semiconductor substrate 12, the GaInNAsSb crystal also has a low bandgap. This allows the semiconductor structure 10 to from an HBT that has a lower turn-on voltage, knee voltage, and base resistance.

Referring again to FIG. 1, the subcollector layer 16, the collector layer 18, the base layer 20, the emitter layer 22, the grading layer 24, and the emitter cap layer 26 are each epitaxial layers formed from different III-V semiconductor materials. The subcollector layer 16 is formed beneath the collector layer 18 and on the semiconductor substrate 12. The subcollector layer 16 is epitaxial so as to be formed from a crystal having a lattice constant that substantially matches the lattice constant of the GaAs crystal of the semiconductor substrate 12. In the embodiment illustrated in FIG. 1, the subcollector layer 16 is formed from another GaAs crystal. As such, since both the subcollector layer 16 and the semiconductor substrate 12 are formed from the same semiconductor material (GaAs), a homojunction 30 is provided between the semiconductor substrate 12 and the subcollector layer 16.

The collector layer 18 is formed on the subcollector layer 16 and is epitaxial so as to be formed from a crystal having a lattice constant that substantially matches the lattice constant of the GaAs crystal forming the semiconductor substrate 12. The crystal of the collector layer 18 may be an Aluminum Gallium Arsenide (AlGaAs) crystal, an Indium Gallium Phosphide (InGaP) crystal, or still another GaAs crystal. A junction 31 is thus formed between the collector layer 18 and the subcollector layer 16. The junction 31 is a heterojunction if the crystal of the collector layer 18 is the AlGaAs crystal or the InGaP crystal. In contrast, the junction 31 is a homojunction if the crystal of the collector layer 18 is another GaAs crystal.

The base layer 20 is formed on the collector layer 18. As mentioned above, the base layer 20 is epitaxial and is formed from the GaInNAsSb crystal having a lattice constant that substantially matches the lattice constant of the GaAs crystal of the semiconductor substrate 12. Since the base layer 20 and the collector layer 18 are formed from different semiconductor materials, a heterojunction 32 is provided between the collector layer 18 and the base layer 20.

The emitter layer 22 is formed on the base layer 20. The emitter layer 22 is epitaxial so as to be formed from a crystal having a lattice constant that substantially matches the lattice constant of the GaAs crystal of the semiconductor substrate 12. The crystal of the emitter layer 22 may be an AlGaAs crystal or an InGaP crystal. Thus, since the emitter layer 22 and the base layer 20 are formed from different semiconductor materials, a heterojunction 34 is provided between the emitter layer 22 and the base layer 20. The grading layer 24 is formed on the emitter layer 22. The grading layer 24 is also epitaxial.

Finally, the emitter cap layer 26 is formed on the grading layer 24. The emitter cap layer 26 is also epitaxial so as to be formed from a crystal. However, the crystal of the emitter cap layer 26 has a lattice constant that does not substantially match the lattice constant of the GaAs crystal that forms the semiconductor substrate 12. Accordingly, the lattice constant of the crystal that forms the emitter layer 22 also does not substantially match the lattice constant of the crystal that forms the emitter cap layer 26. For example, the crystal of the emitter cap layer 26 may be an Indium Gallium Arsenide (InGaAs) crystal. The grading layer 24 is configured to provide a grade between the lattice constant of the InGaAs crystal that forms the emitter cap layer 26 and the lattice constant of the crystal that forms the emitter layer 22. This reduces lattice stresses in the InGaAs crystal of the emitter cap layer 26 and the crystal that forms the emitter layer 22. The functionality of the emitter cap layer 26 is explained in further detail below.

The semiconductor structure 10 shown in FIG. 1 has npn transistor behavior. As mentioned above, the GaInNAsSb crystal that forms the base layer 20 is doped, such that the base layer is p-type. For example, the GaInNAsSb crystal may be doped with a p-type dopant, such as Beryllium (Be), Carbon (C), or a combination of Be and C. In some embodiments, the p-type dopant may have a concentration of approximately between $1 \times 10^{19}$ molecules and $1 \times 10^{20}$ molecules of the p-type dopant per cubic centimeter of the GaInNAsSb crystal forming the base layer 20. For example, a typical concentration is between 1 between $1 \times 10^{19}$ molecules and $5 \times 10^{19}$ molecules of the p-type dopant per cubic centimeter of the GaInNAsSb crystal forming the base layer 20. To provide the npn transistor behavior, the crystal of the collector layer 18 is doped so that the collector layer 18 is n-type. With regard to the emitter layer 22, the crystal of the emitter layer 22 is doped so that the emitter layer 22 is n-type. As such, the majority charge carriers in both the collector layer 18 and the emitter layer 22 are electron-charge carriers.

Each of the subcollector layer 16, the collector layer 18, the base layer 20, the emitter layer 22, and the emitter cap layer 24 has a bandgap. The heterojunctions 32, 34 have characteristic bandgap discontinuities due to the bandgaps of the collector layer 18, the base layer 20, and the emitter layer 22. As explained below, the bandgap discontinuity at the heterojunction 32 may be minimized to increase power efficiency, but it is desirable for there to be some bandgap discontinuity at the heterojunction 34.

The bandgap discontinuity at the heterojunction 34 results from the base layer 20 having a lower bandgap than the bandgap of the emitter layer 22. The bandgap discontinuity at the heterojunction 34 can be divided between a valence band discontinuity and a conduction band discontinuity. Ideally, the bandgap discontinuity at the heterojunction 34 is entirely due to the valence band discontinuity. In this manner, the valence band discontinuity at the heterojunction 34 blocks the reverse injection of holes from the base layer 20 to the emitter layer 22. This configuration allows higher current gain β to be achieved while maintaining dopant concentrations in the emitter layer 22 low and dopant concentrations in the base layer 20 high. In this embodiment, the bandgap of the base layer 20 is between approximately 0.92 electron volts (eV) and 1.04 eV, while the bandgap of the emitter layer 22 is between approximately 1.8 eV and 1.9 eV. The epitaxial growth parameters of the GaInNAsSb can be adjusted to achieve the desired split of the bandgap discontinuity at the heterojunction 34.

The heterojunction 32 between the collector layer 18 and the base layer 20 also has bandgap discontinuity, as mentioned above. Ideally, the bandgap discontinuity at the heterojunction 32 is entirely by a valence band discontinuity, not a conduction band discontinuity. Any conduction band discontinuity can lead to blocking of electrons travelling across the base layer 20 and into the collector layer 18. This electron blocking can lead to increases in the knee voltage of the HBT. Thus, maintaining the conduction band discontinuity at the heterojunction 32 as low as possible results in better power amplifier efficiency.

In this embodiment, the bandgap of the base layer 20 is between approximately 0.92 eV and 1.04 eV, while the emitter layer 22 bandgap is between approximately 1.42 eV and 1.9 eV, depending on the collector layer 18 choice. The epitaxial growth parameters of the GaInNAsSb can also be adjusted to achieve the desired split of the bandgap discontinuity at the heterojunction 32.

As discussed above, the bandgap of the base layer 20 is between approximately 0.92 eV and 1.04 eV. In comparison, semiconductor structures with base layers formed from GaAs have bandgaps of approximately 1.42 eV. Accordingly, the semiconductor structure 10 shown in FIG. 1 lowers the base layer 20 bandgap by about 0.52 eV to 0.38 eV in comparison to semiconductor structures with base layers provided from GaAs. This reduction in the base layer 20 bandgap can result in reduced knee voltages, and thus, in a wider operational range with increased power efficiency.

As discussed above, the HBT is formed with the semiconductor structure 10. The HBT includes an emitter terminus 36 operably associated with the emitter layer 22 so that an emitter of the HBT is provided by the emitter layer 22. In addition, a base terminus 38 is operably associated with the base layer 20 so that a base of the HBT is provided by the base layer 20. Finally, a collector terminus 40 is operably associated with the collector layer 18 so that a collector of the HBT is provided by the collector layer 18. The emitter terminus 36, the base terminus 38, and the collector terminus 40 may each be made from any suitable metallic material such as copper (Cu), Gold (Au), Silver (Ag), Nickel (Ni), and/or the like. The metallic material may also include metallic alloys and other metallic materials mixed with or forming ionic or covalent bonds with other non-metallic materials so as to provide a desired material property.

The HBT is turned on by forward-biasing the heterojunction 34 with a voltage greater than the turn-on voltage. Thus, a voltage difference between a voltage applied to the base terminus 38 and a voltage applied to the emitter terminus 36 has to be greater than the turn-on voltage in order for current to flow between the emitter layer 22 and the base layer 20. To operate in the active mode, the heterojunction 32 should be reverse-biased; thus, the voltage applied to the collector terminus 40 should be greater than both the voltage applied to the base terminus 38 and the voltage applied to the emitter terminus 36. Once the voltage applied to the collector terminus 40 is sufficiently high, a voltage difference between the voltage applied to the collector terminus 40 and the voltage applied to the emitter terminus 36 reaches the knee voltage of the HBT such that the HBT operates in the active region.

The emitter terminus 36, the base terminus 38, and the collector terminus 40 may each be a terminal, a set of terminals, a contact, a set of contacts, or any other part or group of parts for inputting and/or outputting signals from the HBT. These signals may be single-ended radio frequency (RF) signals or differential RF signals. For example, an RF signal may be received at the base terminus 38 so as to be amplified in accordance with a gain of the HBT. The collector terminus 40 and/or the emitter terminus 36 may be coupled to output the RF signal to downstream RF circuitry after amplification by the HBT.

Ideally, the reduction in the bandgap of the base layer 20 is fully translated into a reduction of the knee voltage of the HBT. However, there may be significant degradation of the knee voltage at high frequencies, high loads, and/or at high current densities, and thus, the HBT may experience a soft knee problem. To help compensate for and reduce this degradation, the subcollector layer 16 and the emitter cap layer 26 are provided. The HBT shown in FIG. 1 has a lateral arrangement. Alternatively, the HBT may have a vertical arrangement where the collector terminus 40 is provided on another side of the semiconductor structure 10.

The crystal of the emitter cap layer 26 is doped so that the emitter cap layer 26 is n-type. Furthermore, the emitter cap layer 26 has a higher concentration of doping than the emitter layer 22 to lower the emitter contact resistance. The crystal of the subcollector layer 16 is doped so that the subcollector layer 16 is n-type. However, the subcollector layer 16 has a higher concentration of doping than the collector layer 18. This reduces parasitics and provides a low-resistivity path for current from the base layer 20. This also prevents reductions in the gain of the HBT.

Dimensions of the semiconductor structure 10 may vary in accordance with application requirements. In one embodiment, the semiconductor substrate 12 is anywhere from approximately 10 micrometers to a few hundred micrometers in thickness. The subcollector layer 16, the collector layer 18, the base layer 20, the emitter layer 22, the grading layer 24, and the emitter cap layer 26 are formed epitaxially and may have thicknesses ranging from tens of angstroms to thousands of angstroms. In the embodiment shown in FIG. 1, the base layer 20 has a thickness in a range of between 500 angstroms to 2000 angstroms.

Figure 2:
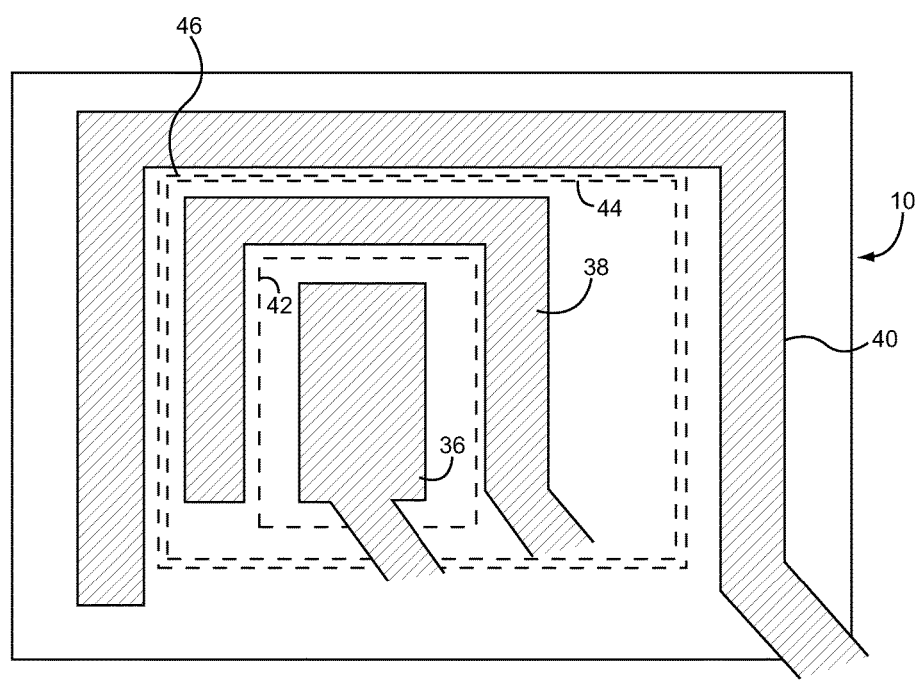
FIG. 2 illustrates a top view of the semiconductor structure shown in FIG. 1, including an emitter terminus, a base terminus, and a collector terminus of the HBT.

FIG. 2 is a top view of the semiconductor structure 10 shown in FIG. 1. The emitter terminus 36, the base terminus 38, and the collector terminus 40 of the HBT are thus shown in accordance with the lateral arrangement. An emitter area 42, a base area 44, and a collector area 46 of the HBT are also shown in FIG. 2. The emitter area 42 is an area of the emitter layer 22 that forms the emitter of the HBT. The base area 44 is an area of the base layer 20 that forms the base of the HBT. Finally, the collector area 46 is an area of the collector layer 18 that provides the collector of the HBT. The emitter area 42, the base area 44, and the collector area 46 may have lengths and widths ranging from less than one micrometer to several hundred micrometers. In this embodiment, the collector area 46 is about the same size and is dimensioned in the same manner as the base area 44.

Note that in alternative embodiments, a plurality of HBTs may be formed with the semiconductor structure 10. In these alternative embodiments, other emitter areas, other base areas, and other collector areas like the emitter area 42, the base area 44, and the collector area 46 may be provided by the emitter layer 22, the base layer 20, and the collector layer 18 to form the emitters, bases, and collectors of the various HBTs. These various HBTs may be arranged laterally or vertically, and some or all of the various HBTs may share emitters, bases, and/or collectors.

Figure 3:
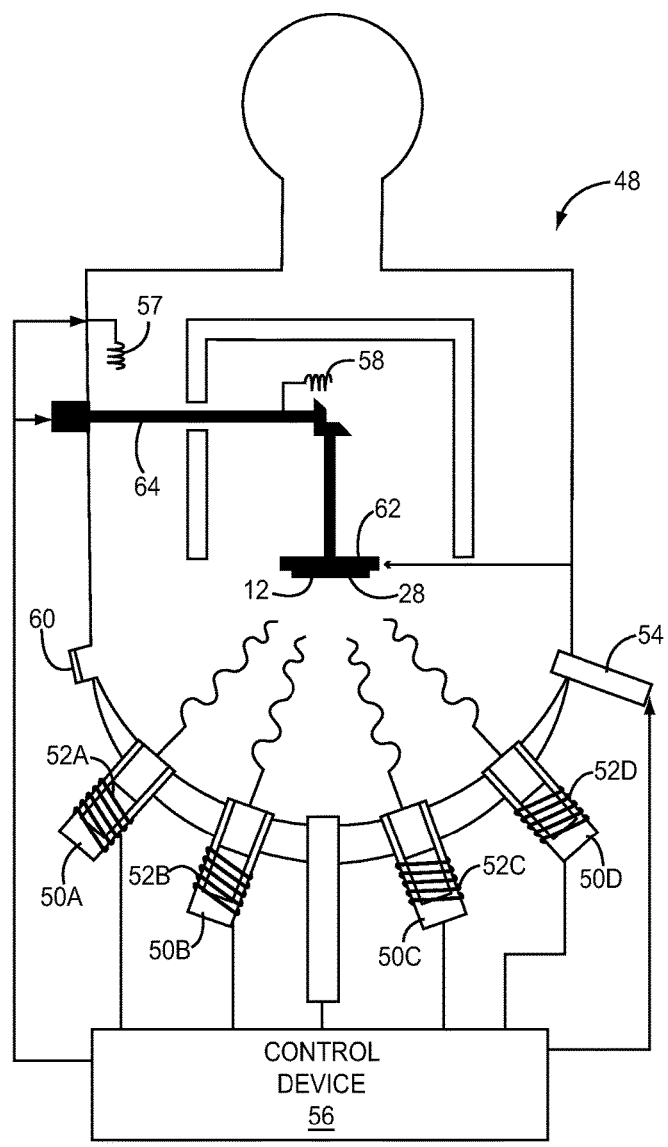
FIG. 3 illustrates one embodiment of a reaction chamber that may be used to form the semiconductor structure shown in FIG. 1 through a Molecular Beam Epitaxy (MBE) process.

FIG. 3 illustrates a reaction chamber 48 that may be utilized to form the semiconductor structure 10 shown in FIG. 1. In FIG. 3, the semiconductor substrate 12 is shown in the reaction chamber 48 prior to forming the subcollector layer 16, the collector layer 18, the base layer 20, the emitter layer 22, the grading layer 24, and the emitter cap layer 26 over the semiconductor substrate 12. To form the subcollector layer 16, the collector layer 18, the base layer 20, the emitter layer 22, the grading layer 24, and the emitter cap layer 26 over the surface 28 of the semiconductor substrate 12, a Molecular Beam Epitaxy (MBE) process is performed within the reaction chamber 48. The reaction chamber 48 has a plurality of effusion cells (referred to generically as element 50, and specifically as elements 50A-50D). Around each of the effusion cells 50 is a heating coil (referred to generically as element 52, and specifically as elements 52A-52D).

Solid elements and compounds, such as Gallium (Ga), Arsenic (As), Indium (In), Aluminum (Al), Nitrogen (N) or nitrides, or Antimony (Ab), along with p-type dopants and n-type dopants, are provided in each of the effusion cells. The elements in the effusion cells 50 are heated until the solid elements begin to sublime. The elements are gaseous after sublimation and condense on the semiconductor substrate 12. During operation, a reflection high energy electron diffractor (RHEED) 54 is configured to monitor the growth of the epitaxial layers. A control device 56 is operable to control heating by the heating coils 52. Furthermore, the control device 56 may control shutters in front of each effusion cell 50 to precisely control a thickness of each epitaxial layer. An ionization gauge 57, a beam flux monitor 58, and a RHEED screen 60 may all be utilized to monitor the crystals grown on the semiconductor substrate 12. As shown in FIG. 3, the semiconductor substrate 12 is provided on a plate 62 in order to form the epitaxial layers. The control device 56 may be configured to operate a mechanical assembly 64 that adjusts an orientation of the semiconductor substrate 12 with respect to the beams from the effusion cells 50.

Figure 4:
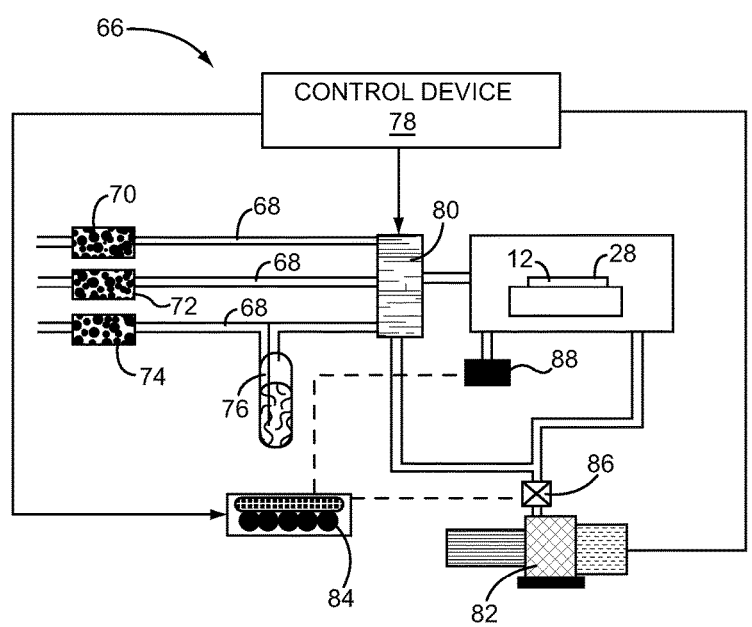
FIG. 4 illustrates another embodiment of a reaction chamber that may be used to form the semiconductor structure shown in FIG. 1 through a Metalorganic Chemical Vapor Deposition (MOCVD) process.

FIG. 4 illustrates another embodiment of a reaction chamber 66. The semiconductor substrate 12 is shown in the reaction chamber 66 prior to forming the subcollector layer 16, the collector layer 18, the base layer 20, the emitter layer 22, the grading layer 24, and the emitter cap layer 26. To form these layers over the surface 28, a Metalorganic Chemical Vapor Deposition (MOCVD) process is performed within the reaction chamber 66. In this embodiment, the reaction chamber 66 has a plurality of inlets 68, each leading to different storage vessels 70, 72, 74. A storage vessel 76 stores an alkyl. A control device 78 operates a run vent assembly 80 to introduce organic compounds, metalorganics, and hydrides from the storage vessels 72, 74, 76. These materials provide a sequence of chemical reactions that grow crystals over the surface 28 of the semiconductor substrate 12. Note that the control device 78 is also operably associated with a vacuum pump 82 so as to pressurize the reaction chamber 66. Additionally, a pressure control system 84 is controlled by the control device 78 to control a throttle bell 86 and a baratron 88 so that the semiconductor substrate 12 is appropriately pressurized for the desired chemical reactions that form epitaxial layers over the surface 28.

Figures 5A, 5B:
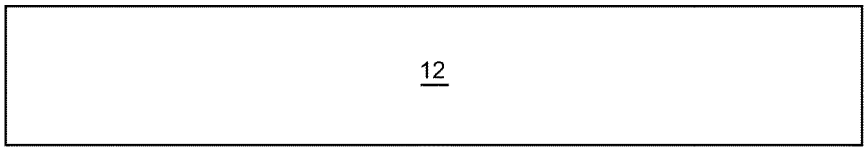
FIGS. 5A-5U illustrate exemplary procedures in one embodiment of a method of forming the semiconductor structure shown in FIG. 1.
Figure 5C:
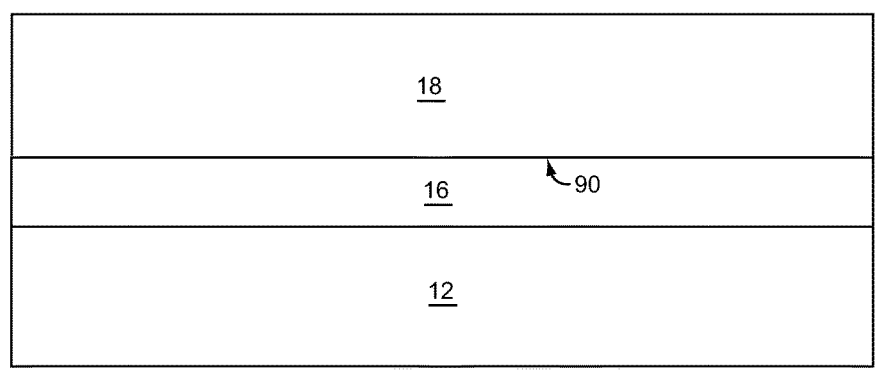
Figure 5D:
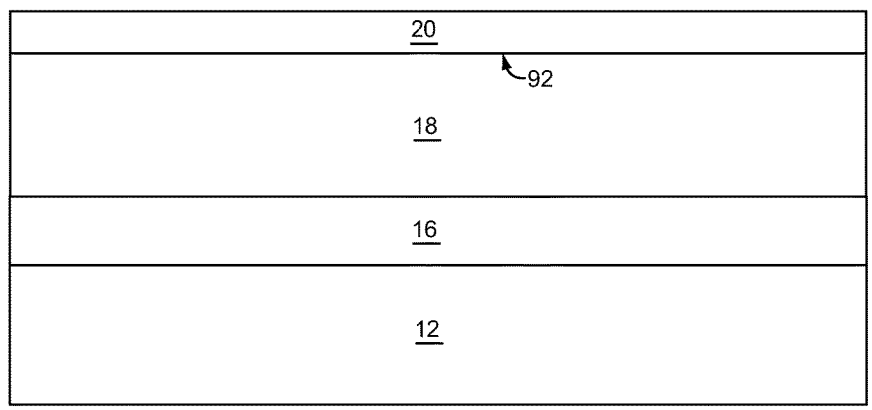
Figure 5E:
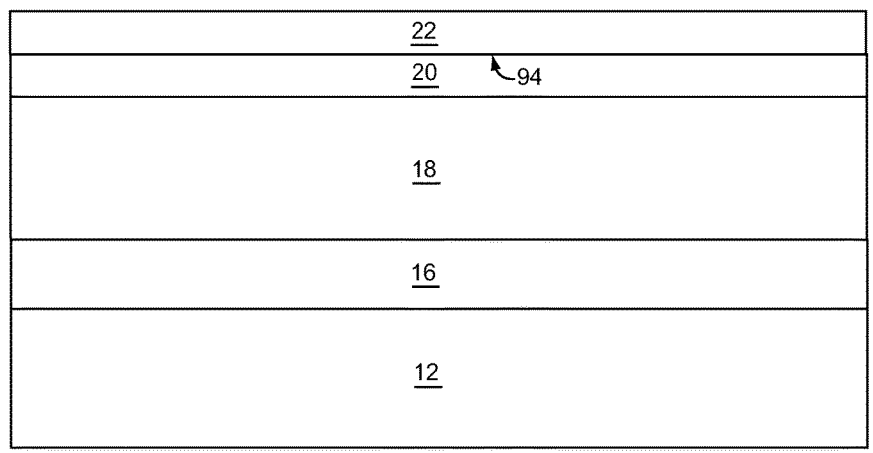
Figure 5F:
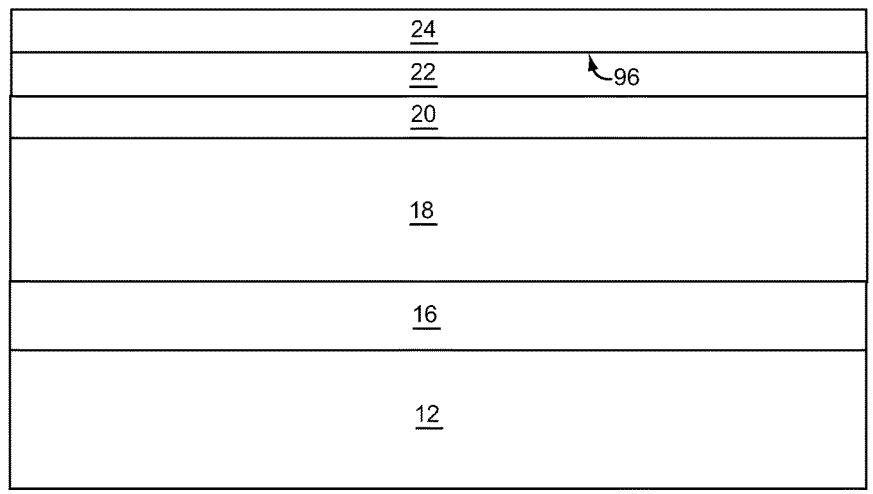
Figure 5G:
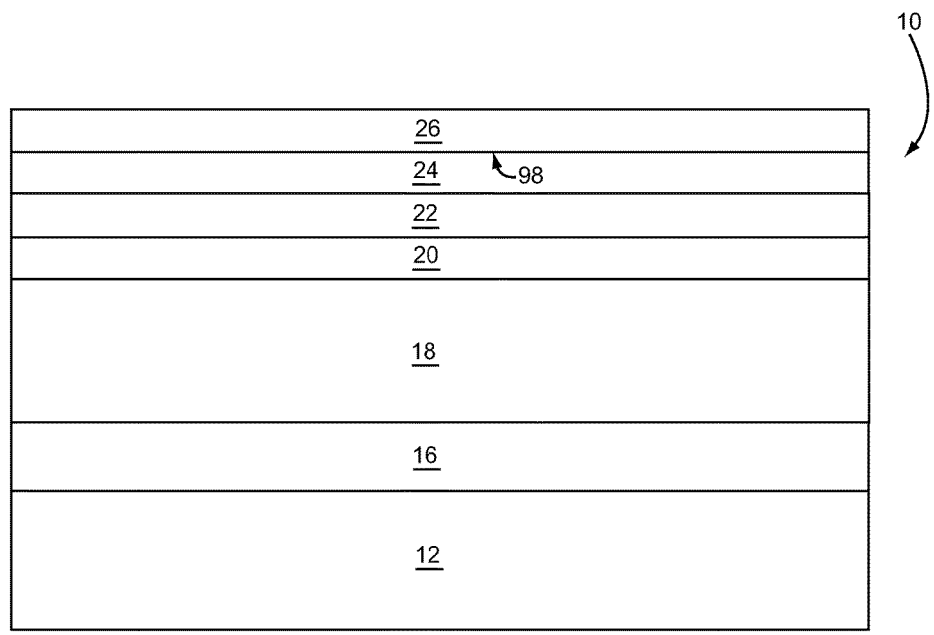
Figure 5H:
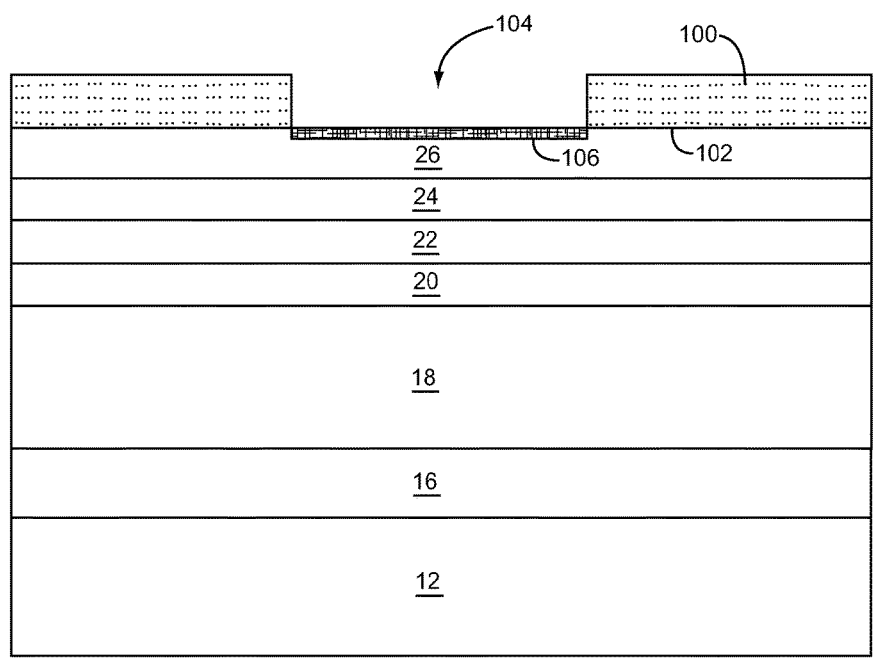
Figure 5I:
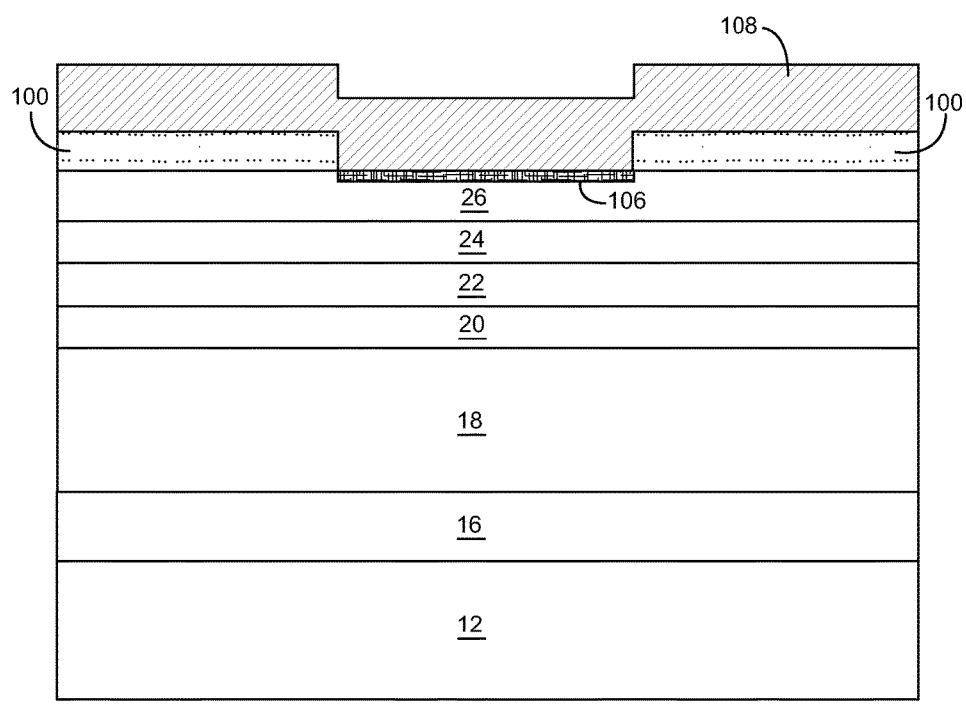
Figure 5J:
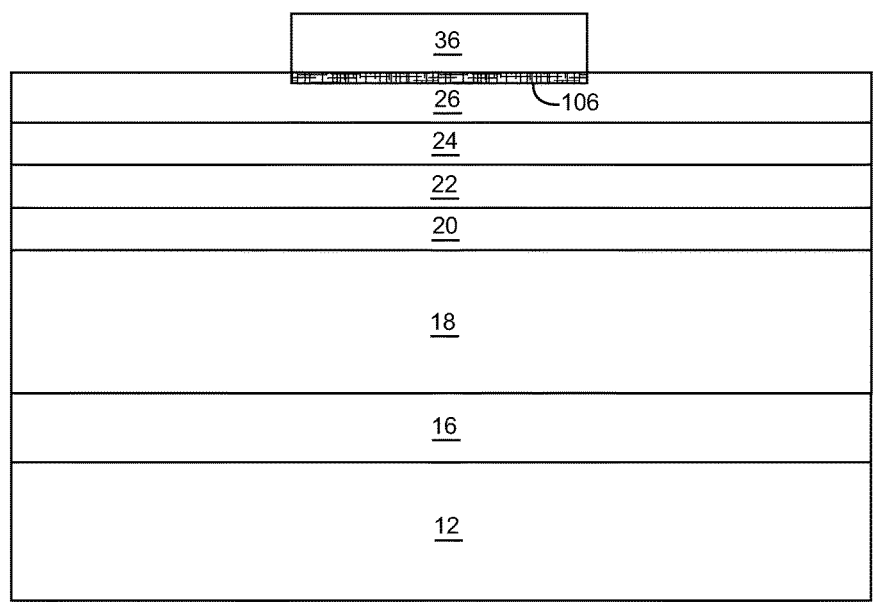
Figure 5K:
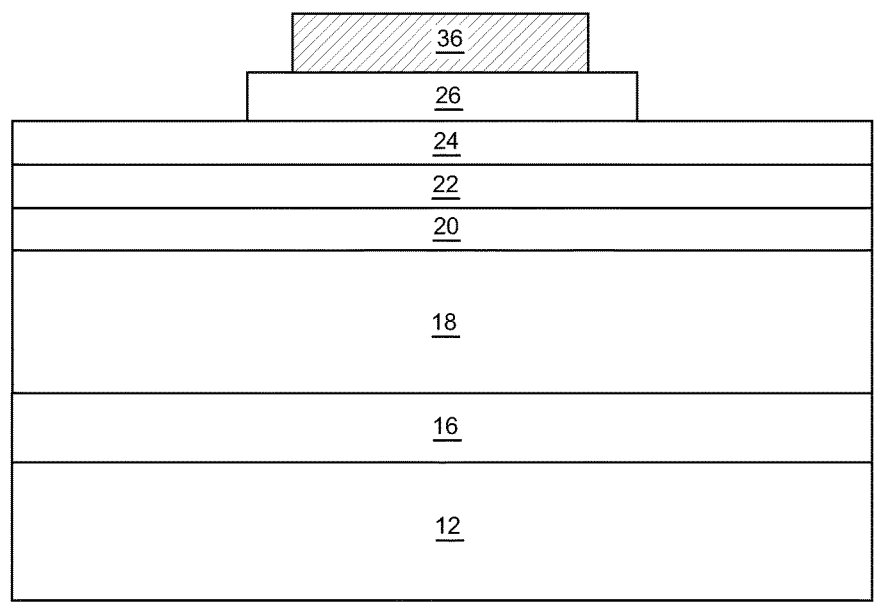
Figure 5L:
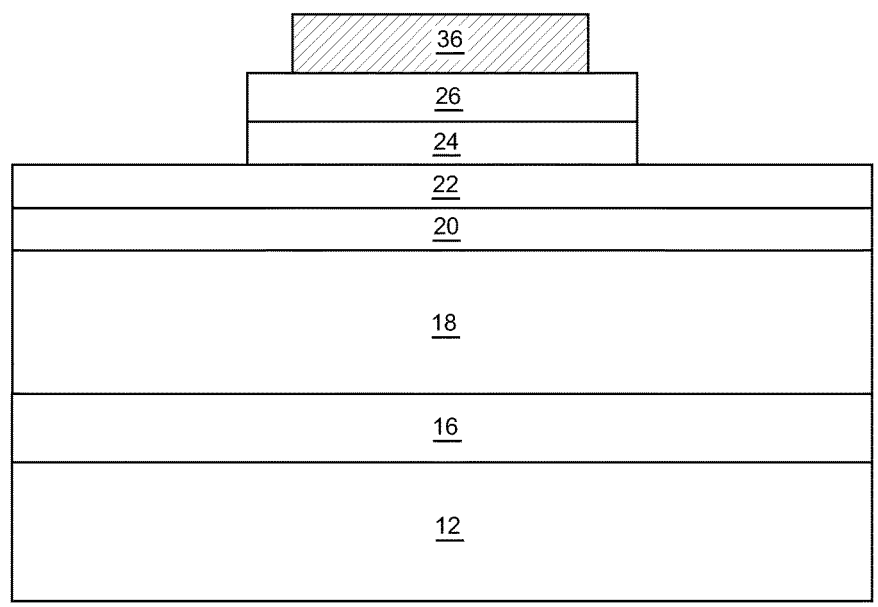
Figure 5M:
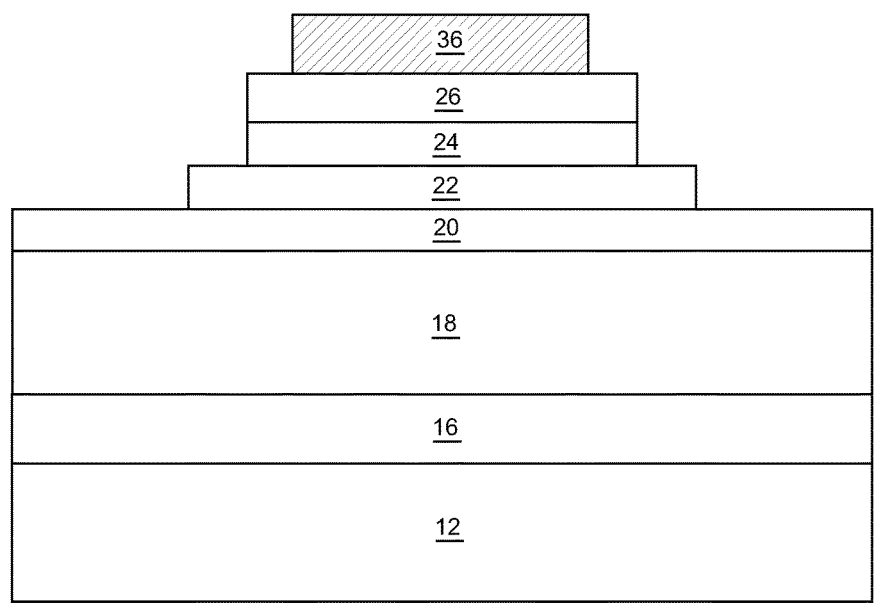
Figure 5N:
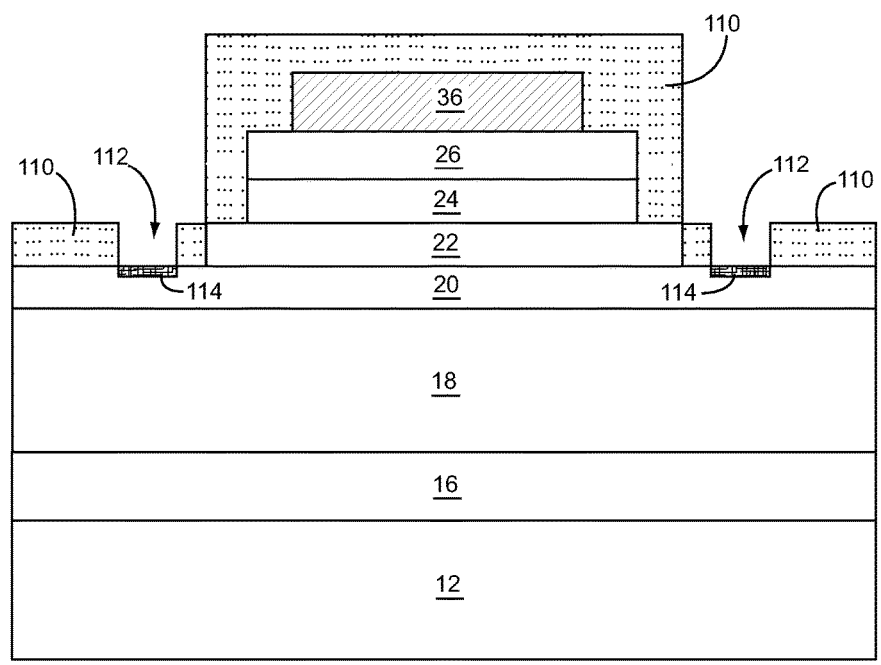
Figure 5O:
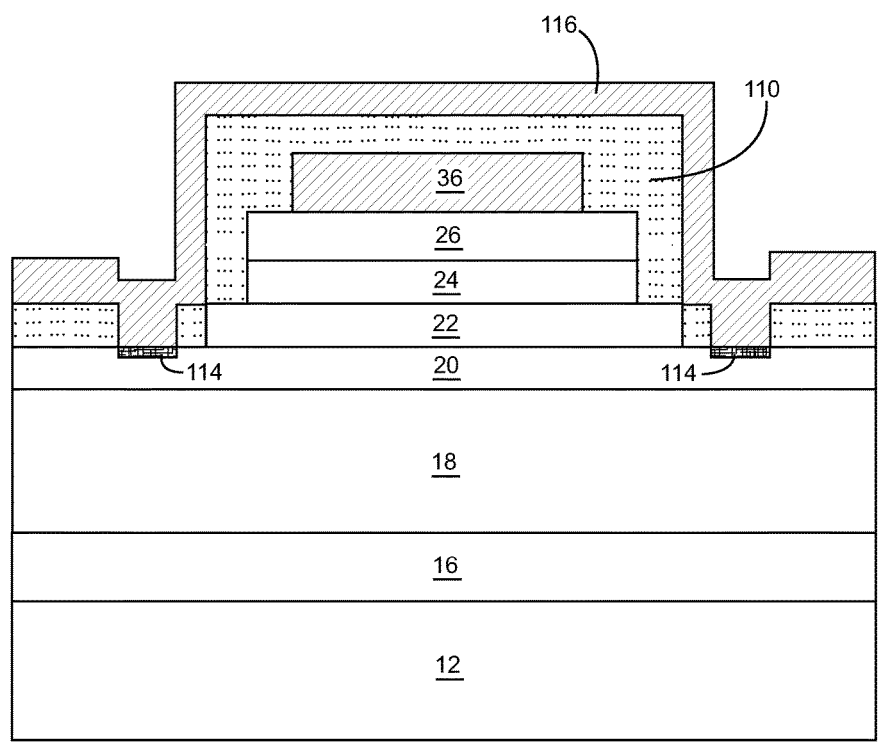
Figure 5P:
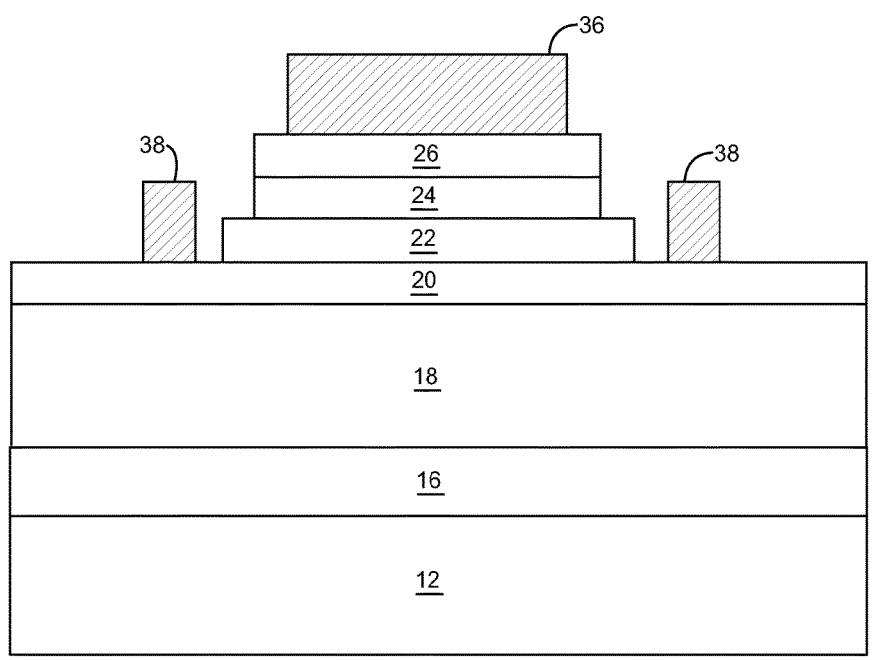
Figure 5Q:
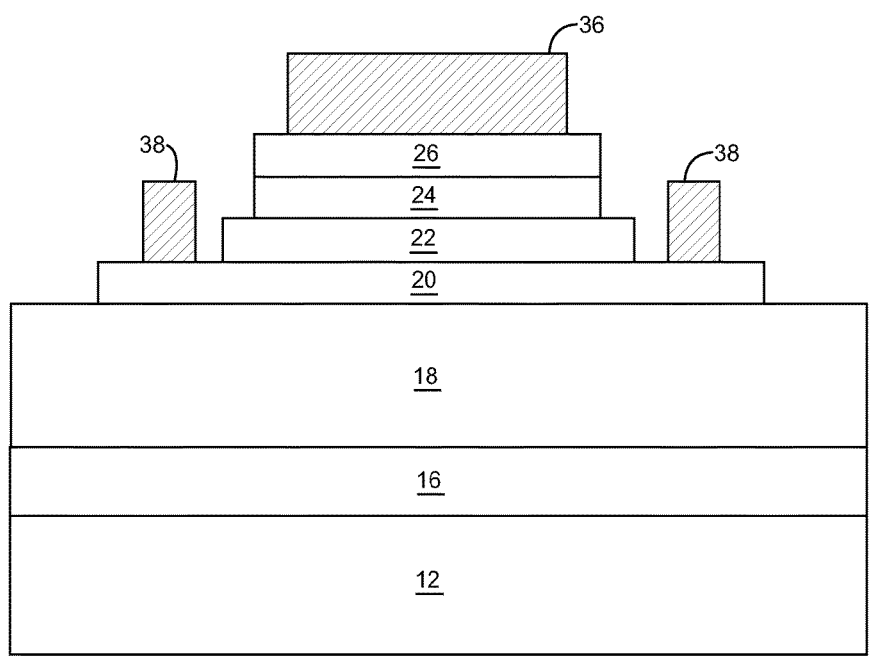
Figure 5R:
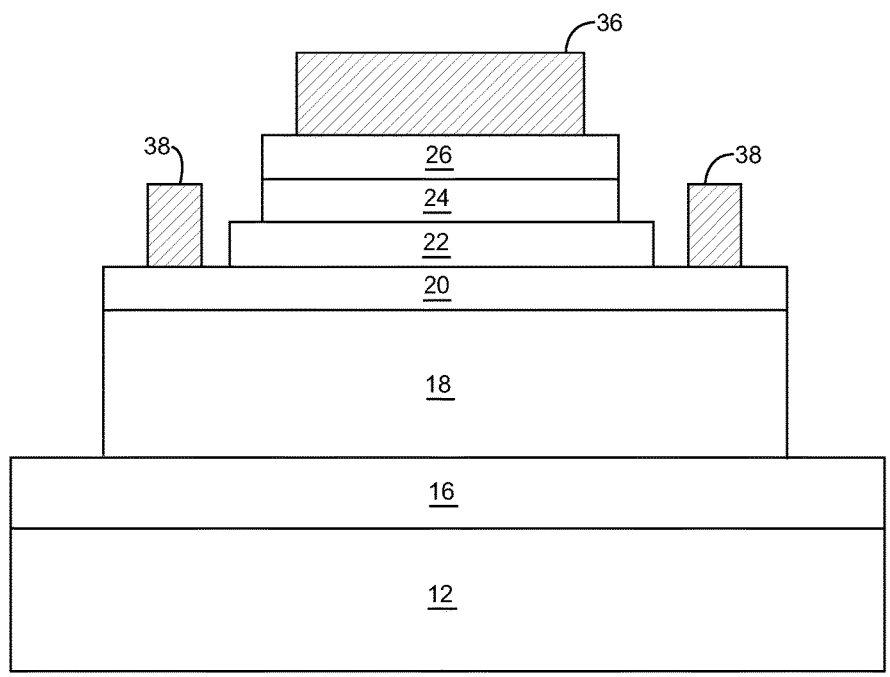
Figure 5S:
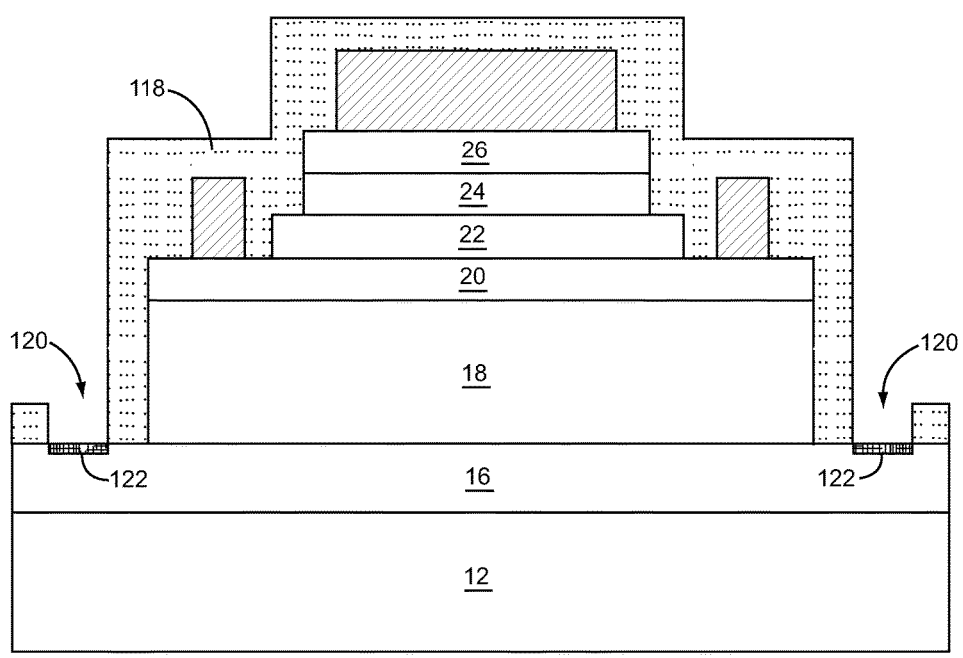
Figure 5T:
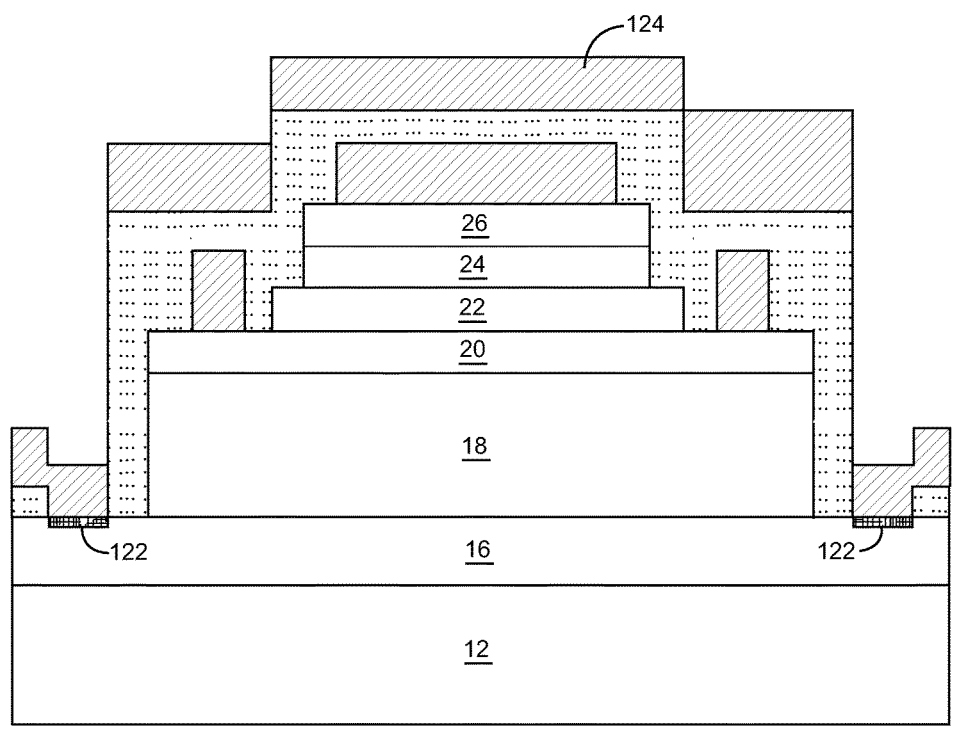
Figure 5U:
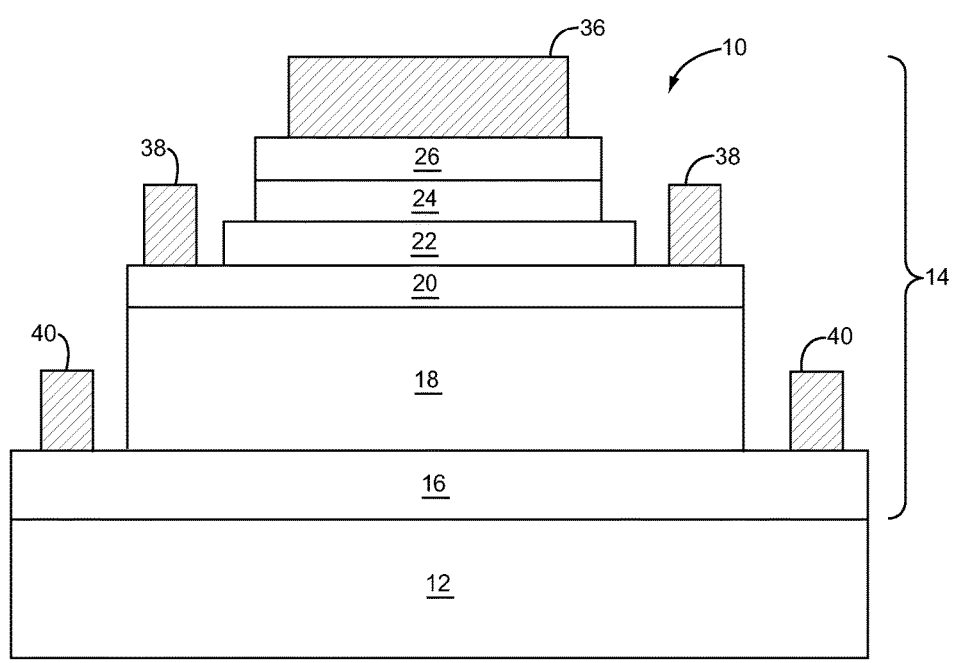

FIGS. 5A-5U illustrate exemplary procedures of one embodiment of a method of forming the semiconductor structure 10 shown in FIG. 1. The exemplary procedures may be implemented through an MBE process within the reaction chamber 48 shown in FIG. 3. Alternatively, the exemplary procedures may be performed through an MOCVD process in the reaction chamber 66 shown in FIG. 4. Note that FIGS. 5A-5U are simply illustrative, and additional or different procedures may be utilized to implement the method, as shall be recognized by those of ordinary skill in the art in light of this disclosure. For example, other deposition techniques besides MBE and MOCVD may be used to form the epitaxial layers.

With regard to the MBE process, sublime elements are transmitted toward the semiconductor substrate 12, but do not react with each other until they reach the wafer, due to a long mean free path of atoms. Although a chemical reaction may take place once the gaseous elements condense over the semiconductor substrate 12, these gaseous elements condense into their crystalline form without, for the most part, additional chemical reagents or precursors. On the other hand, the growth of crystals for the MOCVD process is by chemical reaction, and not by physical deposition. In other words, precursors are deposited through chemical vapor deposition over the semiconductor substrate 12. Another set of precursors needs to be deposited over the original set of precursors so that a chemical reaction will take place over the semiconductor substrate 12 to create the desired crystalline structure.

To begin, the semiconductor substrate 12 formed from GaAs is provided in the reaction chamber 48 or the reaction chamber 66 (FIG. 5A). The semiconductor substrate 12 may be formed by the MBE process or, alternatively, by the MOCVD process. However, this is generally not the case. Typically, the semiconductor substrate 12 is pre-manufactured through other techniques, and thus may be provided by placing simply placing the (pre-manufactured) semiconductor substrate 12 in the reaction chamber 48 or the reaction chamber 66. The semiconductor substrate 12 is formed from a GaAs crystal. Also, the GaAs crystal is not doped, and thus the semiconductor substrate 12 operates as a semi-insulating non-conductive material.

Next, the subcollector layer 16 is formed on the surface 28 and over the semiconductor substrate 12 (FIG. 5B). The subcollector layer 16 is grown epitaxially on the semiconductor substrate 12 so that the subcollector layer 16 is formed as a crystal, where the crystal is doped to be n-type. The subcollector layer 16 may be grown epitaxially through the MBE process, or alternatively, through the MOCVD process.

Next, the collector layer 18 is formed over the semiconductor substrate 12 (FIG. 5C). More specifically, MBE deposition or MOCVD deposition may be used to grow the collector layer 18 epitaxially on a surface 90 of the subcollector layer 16 so that the collector layer 18 is formed as a crystal. The crystal of the collector layer 18 may be any type of crystal that provides sufficient lattice matching to the semiconductor substrate 12. For example, the crystal of the collector layer 18 may be an AlGaAs crystal, an InGaP crystal, or another GaAs crystal. The crystal of the collector layer 18 is doped such that the collector layer 18 is n-type. However, the crystal of the subcollector layer 16 formed prior to forming the collector layer 18 is doped at a higher concentration than the collector layer 18. In this manner, parasitics are reduced and a low resistivity path is provided. These arrangements allow for operation at higher current densities.

The base layer 20 is then formed over the semiconductor substrate 12 such that the base layer 20 is formed from the GaInNAsSb compound (FIG. 5D). In one embodiment, MBE deposition is used to grow the base layer 20 epitaxially on a surface 92 of the collector layer 18 such that the GaInNAsSb compound is a GaInNAsSb crystal. The GaInNAsSb crystal is doped such that the base layer 20 is p-type. In this embodiment, the GaInNAsSb crystal has a non-stochiometric formula of $Ga_{1-x}In_xN_yAs_{1-y-z}Sb_z$, $0.07 \leq x \leq 0.18$, $0.025 \leq y \leq 0.04$, $0.001 \leq z \leq 0.03$. The GaInNAsSb crystal may be doped with Be, C, or a combination of both, and may have a dopant concentration of approximately between $1 \times 10^{19}$ molecules and $1 \times 10^{20}$ molecules of the p-type dopant per cubic centimeter of the GaInNAsSb crystal. The base layer 20 may be grown to have a thickness in a range between approximately 500 angstroms and 2000 angstroms. As discussed above, the use of the GaInNAsSb crystal for the base layer 20 is advantageous, since the lattice constant of the GaInNAsSb crystal substantially matches the lattice constant of the GaAs crystal forming the semiconductor substrate 12, and due to the reduced bandgap provided by the GaInNAsSb crystal. Alternatively, MOVCD deposition may be performed to grow the base layer 20 epitaxially.

Next, MBE deposition may be used to form the emitter layer 22 over the semiconductor substrate 12 (FIG. 5E). More specifically, MBE deposition grows the emitter layer 22 epitaxially on a surface 94 of the base layer 20 such that the emitter layer 22 is formed as a crystal. The crystal may be formed as any suitable crystal that has a lattice constant that matches the lattice constant of the GaAs crystal that forms the semiconductor substrate 12. For example, the crystal of the emitter layer 22 may be an AlGaAs crystal or an InGaP crystal. The crystal of the emitter layer 22 is doped such that the emitter layer is n-type. Alternatively, the emitter layer 22 may be grown epitaxially through MOCVD deposition.

Next, MBE deposition may be used to form the grading layer 24 over the semiconductor substrate 12 (FIG. 5F). In particular, MBE deposition grows the grading layer 24 on a surface 96 of the emitter layer 22 such that the grading layer 24 is formed as a crystal with a superlattice structure. Alternatively, the grading layer 24 may be grown through MOCVD deposition. MBE deposition then forms the emitter cap layer 26 over the semiconductor substrate 12 (FIG. 5G). More specifically, MBE deposition grows the emitter cap layer 26 epitaxially on a surface 98 of the grading layer 24 such that the emitter cap layer 26 is formed as a crystal. For example, the crystal of the emitter cap layer 26 may be an InGaAs crystal doped so that the emitter cap layer 26 is n-type. However, the emitter cap layer 26 is doped at a higher concentration than the emitter layer 22. The InGaAs crystal is used to form the emitter cap layer 26 because its lattice can support this higher concentration of n-type doping and it has a small bandgap. However, the lattice constant of the InGaAs crystal does not substantially match the lattice constant of the semiconductor substrate 12, and thus also the lattice constant of the crystal that forms the emitter layer 22. As such, the grading layer 24 is configured to provide a grade between the crystal of the emitter layer 22 and the InGaAs crystal of the emitter cap layer 26. Alternatively, the emitter cap layer 26 may be grown through MOCVD deposition. After the procedure described with regard to FIG. 5G, the semiconductor structure 10 may be removed and sent or sold to another manufacturer. In this manner, the semiconductor structure 10, as shown in FIG. 5G, may be sold so that integrated circuit manufacturers can form any desired semiconductor device or semiconductor devices with the semiconductor structure 10.

Referring now to FIGS. 5H-5U, the procedures described in FIGS. 5H-5U are related to forming the HBT shown in FIG. 1 on the semiconductor structure 10. However, these procedures are simply exemplary, and other procedures may be implemented to form the HBT and/or other types of semiconductor devices. FIGS. 5H-5M describe procedures for forming the emitter of the HBT. Initially, a mask 100 is provided on a surface 102 of the emitter cap layer 26 (FIG. 5H). The mask 100 has an opening 104 which may be provided through photolithography. An area 106 of the emitter cap layer 26 is exposed through the opening 104 of the mask 100. A first metallic layer 108 is then provided over the mask 100, in the opening 104 (shown in FIG. 5H), and on the area 106 of the emitter cap layer 26 (FIG. 5I). Portions of the first metallic layer 108 are removed so that the first metallic layer 108 is shaped into the emitter terminus 36 (FIG. 5J). This may be done by lifting off the mask 100 (shown in FIG. 5I) through well-known lift-off techniques. The emitter terminus 36 in this embodiment is provided on the area 106 of the emitter cap layer 26. In this manner, the emitter terminus 36 is operably associated with the emitter layer 22 so that the emitter of the HBT is provided by the emitter layer 22. To form the emitter mesa, the emitter cap layer 26 is etched (FIG. 5K). Then, the grading layer 24 is etched (FIG. 5L). Finally, the emitter layer 22 is etched so that the emitter of the HBT has the emitter area 42 (shown in FIG. 2) and to expose the base layer 20 along a perimeter of the emitter area 42 (FIG. 5M).

FIGS. 5N to 5Q relate to procedures for forming the base of the HBT with the base layer 20. Initially, a mask 110 is provided over the semiconductor substrate 12 (FIG. 5N). The mask 110 may be shaped through photolithography to define an opening 112 that exposes an area 114 of the base layer 20. A second metallic layer 116 is provided over the base layer 20 (FIG. 5O). In this manner, the metallic layer 116 fills the opening 112 (shown in FIG. 5N) and contacts the area 114 of the base layer 20. Next, portions of the second metallic layer 116 are removed, so that the second metallic layer 116 is shaped into the base terminus 38 (FIG. 5P). This may be done by lifting off the mask 110 (shown in FIG. 5O) through well-known lift-off techniques. The base terminus 38 is thus operably associated with the base layer 20 so that the base of the HBT is provided by the base layer 20. Subsequently, the base layer 20 is etched so that the base of the HBT has the base area 44 (shown in FIG. 2) and to expose the collector layer 18 along a perimeter of the base area 44 (FIG. 5Q).

FIGS. 5R to 5T relate to procedures for forming the collector of the HBT with the collector layer 18. Initially, the collector layer is etched so that the collector of the HBT has the collector area 46 (shown in FIG. 2) and to expose the subcollector layer 16 along a perimeter of the collector area 46 (FIG. 5R). A mask 118 is then formed over the semiconductor substrate 12 (FIG. 5S). The mask 118 may be shaped by photolithography so as to have an opening 120 that exposes an area 122 of the subcollector layer 16. A third metallic layer 124 is formed over the subcollector layer 16 (FIG. 5T). The third metallic layer 124 thus fills the opening 120 (shown in FIG. 5S) so as to be provided on the area 122 of the subcollector layer 16. Portions of the third metallic layer 124 are then removed so that the third metallic layer 124 is shaped into the collector terminus 40. In this manner, the collector terminus 40 is operably associated with the collector layer 18 so that the collector of the HBT is provided by the collector layer 18. As shown in FIG. 5U, the semiconductor structure 10 has been formed so that the epitaxial region 14 provides the HBT in the lateral configuration.

Those skilled in the art will recognize improvements and modifications to the preferred embodiments of the present disclosure. All such improvements and modifications are considered within the scope of the concepts disclosed herein and the claims that follow.

What is claimed is:

1. A heterojunction bipolar transistor (HBT) comprising:
   a semiconductor substrate formed from a Gallium Arsenide (GaAs) having a first lattice constant;
   a base layer formed over the semiconductor substrate, wherein the base layer is epitaxial so as to be formed from a Gallium Indium Nitride Arsenide Antimonide (GaInNAsSb) crystal having a second lattice constant and having a first bandgap, wherein the second lattice constant substantially matches the first lattice constant of the GaAs crystal and wherein the GaInNAsSB crystal is doped such that the base layer is p-type;
   a collector layer formed over the semiconductor substrate, wherein the collector layer is epitaxial so as to be formed from a third crystal having a third lattice constant that substantially matches the first lattice constant of the GaAs crystal, and wherein the third crystal is doped such that the collector layer is n-type and the base layer is formed on the collector layer so that a first heterojunction of the HBT is provided between the collector layer and so that the first heterojunction has first bandgap discontinuity;
   an emitter layer formed over the semiconductor substrate wherein the emitter layer is epitaxial so as to be formed from an Indium Gallium Arsenide (InGaAs) crystal having a fourth lattice constant that substantially matches the first lattice constant of the GaAs crystal and wherein the InGaAs crystal is doped such that the emitter layer is n-type and the base layer is formed on the emitter layer so that a second heterojunction of the HBT is provided between the base layer and the emitter layer and so that the second heterojunction of the HBT has a second bandgap discontinuity, wherein the first bandgap discontinuity and the second bandgap discontinuity define a turn on voltage of the HBT and a knee voltage of the HBT;
   an emitter cap layer formed over the emitter layer, the emitter cap layer being epitaxial so as to be formed from a fifth crystal, wherein the fifth crystal is doped so that the emitter cap layer is n-type, but such that doping is at a higher concentration than at the emitter layer; and
   a subcollector layer formed beneath the collector layer, the subcollector layer being epitaxial so as to be formed from a sixth crystal, wherein the sixth crystal is doped so that the subcollector layer is n-type, but such that doping is at a higher concentration than at the collector layer.

2. The HBT of claim 1 wherein the GaInNAsSB crystal and the third crystal are configured to provide the first heterojunction such that the first bandgap discontinuity only includes a first valence bandgap discontinuity, and wherein the third crystal and the InGaAs crystal are configured such that the second bandgap discontinuity is divided between a second valence band discontinuity and a first conduction band discontinuity.

3. The HBT of claim 2 wherein the third crystal is selected from a group consisting of Aluminum Gallium Arsenide (AlGaAs) crystal and an Indium Gallium Phosphide (InGaP) crystal.

4. The HBT of claim 2 wherein the GaAs crystal is not doped.

* * * * *

UNITED STATES PATENT AND TRADEMARK OFFICE
CERTIFICATE OF CORRECTION

| | |
|---|---|
| PATENT NO. | : 9,761,678 B2 |
| APPLICATION NO. | : 13/655659 |
| DATED | : September 12, 2017 |
| INVENTOR(S) | : Brian G. Moser and Michael T. Fresina |

Page 1 of 1

It is certified that error appears in the above-identified patent and that said Letters Patent is hereby corrected as shown below:

In the Claims

In Column 11, Line 58, replace "Arsenide (GaAs) having" with --Arsenide (GaAs) crystal having--.

In Column 12, Line 7, replace "GalnNAsSB" with --GaInNAsSB--.

Signed and Sealed this
Thirty-first Day of October, 2017

Joseph Matal
*Performing the Functions and Duties of the*
*Under Secretary of Commerce for Intellectual Property and*
*Director of the United States Patent and Trademark Office*